United States Patent
Feucht et al.

(10) Patent No.: US 6,649,565 B1
(45) Date of Patent: Nov. 18, 2003

(54) SELECTIVE HERBICIDES ON THE BASIS OF A SUBSTITUTED PHENYLSULFONYL-AMINOCARBONYLTRIAZOLINONE AND SAFENERS

(75) Inventors: Dieter Feucht, Monheim (DE); Peter Dahmen, Neuss (DE); Mark Wilhelm Drewes, Langenfeld (DE); Birgit Krauskopf, Leawood, KS (US); Mathias Kremer, Burscheid (DE); Rolf Pontzen, Leichlingen (DE); Hans-Joachim Santel, Leverkusen (DE); Arndt Wellmann, Odenthal (DE); Joachim Kluth, Langenfeld (DE); Klaus-Helmut Müller, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/069,350

(22) PCT Filed: Aug. 16, 2000

(86) PCT No.: PCT/EP00/07982

§ 371 (c)(1),
(2), (4) Date: Mar. 26, 2002

(87) PCT Pub. No.: WO01/15533

PCT Pub. Date: Mar. 8, 2001

(30) Foreign Application Priority Data

Aug. 27, 1999 (DE) .......................... 199 40 860

(51) Int. Cl.[7] .................. A01N 25/32; A01N 47/38
(52) U.S. Cl. .................. 504/105; 504/107; 504/274
(58) Field of Search ................. 504/103, 104, 504/105, 106, 107, 108, 109, 110, 111, 112, 273

(56) References Cited

U.S. PATENT DOCUMENTS

| | | | |
|---|---|---|---|
| 4,639,266 A | 1/1987 | Heubach et al. | 71/92 |
| 4,881,966 A | 11/1989 | Nyffeler et al. | 71/94 |
| 5,534,486 A | 7/1996 | Müller et al. | 504/273 |
| 5,700,758 A | 12/1997 | Rösch et al. | 504/106 |
| 5,703,008 A | 12/1997 | Rösch et al. | 504/106 |
| 6,162,762 A | 12/2000 | Cornes et al. | 504/105 |

FOREIGN PATENT DOCUMENTS

| | | |
|---|---|---|
| DE | 196 38 887 | 3/1998 |
| EP | 0 112 799 | 7/1984 |
| EP | 0 507 171 | 10/1992 |
| EP | 0 931 456 | 7/1999 |
| WO | 99/57983 | 11/1999 |

OTHER PUBLICATIONS

Devine et al. Physiology of Herbicide Action. Chapter 17.4 "Safeners for herbicides". p. 376–387. 1993.*

Scoggan, A.C. et al: "Bay MKH 6561: a new herbicide for grass and broadleaf weed control in cereals." Brighton Conf..—Weeds (1999), (vol. 1), 93–98, XP000978388 Seite 93, die Zusammenfassung, Seite 97, letzter Absatz–Seite 98.

Feucht, D. et al: "Bay MKH 6561—a new selective herbicide for grass control in wheat, rye and triticale." Proc. Br. Crop. Prot. Conf. Weeds (1999, vol. 1, 53–58) 2 Fig. 4 Tab. 1 Ref. Coden: PBCWDF, XP000097839, Seite 53, die Zusammenfassung, Seite 57, letzter Absatz—Seite 58.

Bell, C.E.: "Field evaluation of MKH—6561 for Phalaris Minor control in durum wheat." Proc. Br. Crop. Prot. Conf. Weeds (1999, vol. 1, 211–16) 5 Tab. 10 Ref. Coden: PBCWDF, XP000978387, Univ. California Seite 211, die Zusammenfassung, Seite 213.

* cited by examiner

*Primary Examiner*—S. Mark Clardy
(74) *Attorney, Agent, or Firm*—Richard E. L. Henderson; John E. Mrozinski, Jr.

(57) ABSTRACT

Selective herbicidal compositions are provided which comprise an effective amount of an active compound combination comprising 2-(2-methoxycarbonyl-phenylsulphonylaminocarbonyl)-4-methyl-5-propoxy-2, 4-dihydro-3H-1,2,4-triazol-3-one of the formula (I)

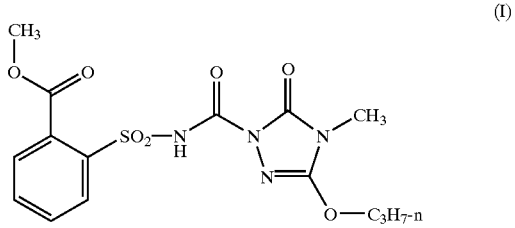

(I)

and/or one or more salts of the compound of the formula (I), in particular the sodium salt and at least one crop plant compatibility-improving compound as described herein.

9 Claims, No Drawings

US 6,649,565 B1

SELECTIVE HERBICIDES ON THE BASIS OF A SUBSTITUTED PHENYLSULFONYL-AMINOCARBONYLTRIAZOLINONE AND SAFENERS

FIELD OF THE INVENTION

The invention relates to novel selective herbicidal active compound combinations comprising, on the one hand, 2-(2-methoxycarbonyl-phenylsulphonylaminocarbonyl)-4-methyl-5-propoxy-2,4-dihydro-3H-1,2,4-triazol-3-one and/or its salts, in particular its sodium salt, and, on the other hand, at least one compound which improves crop plant compatibility and which can be used particularly successfully for the selective control of weeds in various crops of useful plants.

BACKGROUND OF THE INVENTION

Substituted phenylsulphonylaminocarbonyl-triazolinones are known as effective herbicides (cf., for example, EP-A 507 171). However, the activity of these compounds and/or their compatibility with crop plants are not entirely satisfactory under all conditions.

Furthermore, active compound combinations of substituted phenylsulphonylaminocarbonyl-triazolinones and other herbicidally active compounds for obtaining a synergistic effect (cf. DE-A 196 388 87) have been disclosed. However, the use properties of these combination products are likewise not entirely satisfactory under all conditions. The combination of a 2-(2-trifluoromethoxy-phenylsulphonylaminocarbonyl)-4-methyl-5-methoxy-3H-1,2,4-triazol-3-one with certain safeners has been also described in the EP-A 931 456.

DETAILED DESCRIPTION OF THE INVENTION

Surprisingly, it has now been found that 2-(2-methoxycarbonyl-phenylsulphonylaminocarbonyl)-4-methyl-5-propoxy-2,4-dihydro-3H-1,2,4-triazol-3-one and/or its salts, when used together with the compounds described further below which improve crop plant compatibility (safener/antidotes) prevent damage to the crop plants extremely well and can be used particularly advantageously as a broad-spectrum combination preparation for the selective control of weeds in crops of useful plants, such as, for example, in cereals.

The present invention provides selective herbicidal compositions, characterized in that they comprise an active compound combination comprising
(a) 2-(2-methoxycarbonyl-phenylsulphonylaminocarbonyl)-4-methyl-5-propoxy-2,4-dihydro-3H-1,2,4-triazol-3-one of the formula (I)

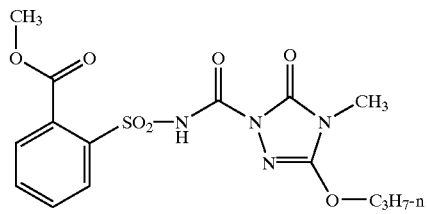

(I)

and/or one or more salts of the compound of the formula (I), in particular the sodium salt, and (b) at least one crop plant compatibility-improving compound from the following group of compounds:
α-(1,3-dioxolan-2-yl-methoximino)-phenylacetonitrile (oxabetrinil), α-(cyano-methoximino)-phenylacetonitrile (cyometrinil), 4-chloro-N-(1,3-dioxolan-2-yl-methoxy)-α-trifluoro-acetophenone oxime (fluxofenim), 4,6-dichloro-2-phenyl-pyrimidine (fenclorim), 4-dichloroacetyl-3,4-dihydro-3-methyl-2H-1,4-benzox-azine (benoxacor), 1-methyl-hexyl 5-chloro-quinoxaline-8-oxyacetate (clo-quintocet), 2,2-dichloro-N-(2-oxo-2-(2-propenylamino)-ethyl)-N-(2-propenyl)-acetamide (DKA-24), 1,8-naphthalic anhydride, ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 3-dichloroacetyl-5-(2-furanyl)-2,2-dimethyl-oxazolidine (furilazole, MON-13900), 4-dichloroacetyl-1-oxa-4-aza-spiro[4.5]-decane (AD-67), 2-dichloro-methyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylamino-carbonylamino)-benzenesulphonamide and/or the compounds below, defined by general formulae

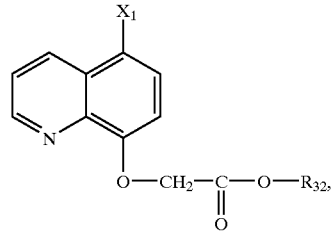

(IIa)

in which
$R_{32}$ represents hydrogen, $C_1$–$C_8$-alkyl or $C_1$–$C_6$-alkoxy- or $C_3$–$C_6$-alkenyloxy-substituted $C_1$–$C_8$-alkyl and
$X_1$ represents hydrogen or chlorine;
or of the formula (IIb)

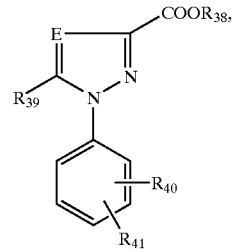

(IIb)

in which
E represents nitrogen or methine;
$R_{38}$ represents $C_1$–$C_4$-alkyl;
$R_{39}$ represents —$CCl_3$, phenyl or halogen-substituted phenyl, and
$R_{40}$ and $R_{41}$ independently of one another each represent hydrogen or halogen;

or of the formula (IIc)

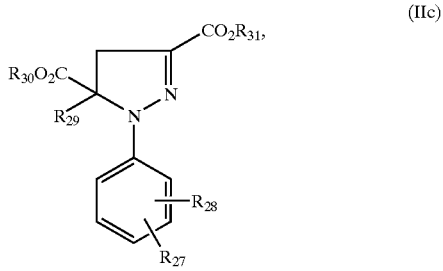

in which
R$_{27}$ and R$_{28}$ independently of one another each represent hydrogen or halogen and
R$_{29}$, R$_{30}$ and R$_{31}$ independently of one another each represent C$_1$–C$_4$-alkyl;
or of the formula (IId)

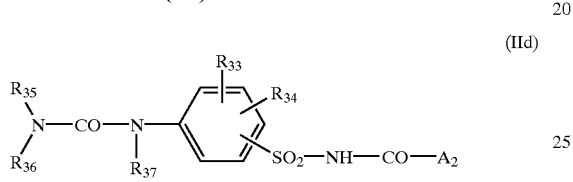

in which
A$_2$ represents a group

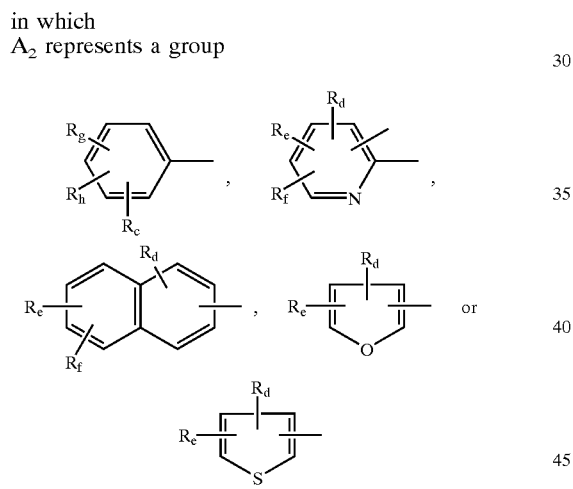

R$_{35}$ and R$_{36}$ independently of one another each represents hydrogen, C$_1$–C$_8$-alkyl, C$_3$–C$_8$-cycloalkyl, C$_3$–C$_6$-alkenyl, C$_3$–C$_6$-alkinyl,

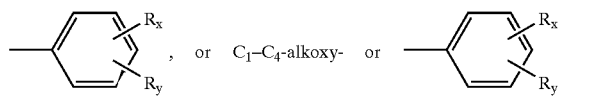

, or C$_1$–C$_4$-alkoxy- or substituted C$_1$–C$_4$-alkyl; or
R$_{35}$ and R$_{36}$ together form a C$_4$–C$_6$-alkylene bridge which may be interrupted by oxygen, sulphur, SO, SO$_2$, NH or —N(C$_1$–C$_4$-alkyl)-;
R$_{37}$ represents hydrogen or C$_1$–C$_4$-alkyl;
R$_{33}$ represents hydrogen, halogen, cyano, trifluoromethyl, nitro, C$_1$–C$_4$-alkyl, C$_1$–C$_4$-alkoxy, C$_1$–C$_4$-alkylthio, C$_1$–C$_4$-alkylsulphinyl, C$_1$–C$_4$-alkylsulphonyl, —COOR$_j$, —CONR$_k$R$_m$, —COR$_n$, —SO$_2$—NR$_k$R$_m$ or —OSO$_2$—C$_1$–C$_4$-alkyl;
R$_g$ represents hydrogen, halogen, cyano, nitro, C$_1$–C$_4$-alkyl, C$_1$–C$_4$-halogenoalkyl, C$_1$–C$_4$-alkylthio, C$_1$–C$_4$-alkylsulphinyl, C$_1$–C$_4$-alkylsulphonyl, —COOR$_j$, —CONR$_k$R$_m$, —COR$_n$, —SO$_2$NR$_k$R$_m$, —OSO$_2$—C$_1$–C$_4$-alkyl, C$_1$–C$_6$-alkoxy or C$_1$–C$_6$-alkoxy which is substituted by C$_1$–C$_4$-alkoxy or halogen, C$_3$–C$_5$-alkenyloxy or C$_3$–C$_6$-alkenyloxy which is substituted by halogen, or represents C$_3$–C$_6$-alkinyloxy or
R$_{33}$ and R$_{34}$ together form a C$_3$–C$_4$-alkylene bridge which may be substituted by halogen or C$_1$–C$_4$-alkyl, or form a C$_3$–C$_4$-alkenylene bridge which may be substituted by halogen or C$_1$–C$_4$-alkyl, or form a C3–C$_4$-alkadienylene bridge which may be substituted by halogen or C$_1$–C$_4$-alkyl;
R$_{34}$ and R$_h$ independently of one another each represent hydrogen, halogen, C$_1$–C$_4$-alkyl, trifluoromethyl, C$_1$–C$_6$-alkoxy, C$_1$–C$_6$-alkylthio or —COOR$_j$;
R$_c$ represents hydrogen, halogen, nitro, C$_1$–C$_4$-alkyl or methoxy,
R$_d$ represents hydrogen, halogen, nitro, C$_1$–C$_4$-alkyl, C$_1$–C$_4$-alkoxy, C$_1$–C$_4$-alkylthio, C$_1$–C$_4$alkylsulphinyl, C$_1$–C$_4$alkylsulphonyl, —COOR$_j$ or CONR$_k$R$_m$;
R$_e$ represents hydrogen, halogen, C$_1$–C$_4$-alkyl, —COOR$_j$, trifluoromethyl or methoxy, or
R$_d$ and Re together form a C$_3$–C$_4$-alkylene bridge;
R$_f$ represents hydrogen, halogen or C$_1$–C$_4$-alkyl;
R$_x$ and R$_y$ independently of one another each represent hydrogen, halogen, C$_1$–C$_4$-alkyl, C$_1$–C$_4$-alkoxy, C$_1$–C$_4$-alkylthio, —COOR$_{38}$, trifluoromethyl, nitro or cyano;
R$_j$, R$_k$ and R$_m$ independently of one another each represent hydrogen or C$_1$–C$_4$-alkyl; or
R$_k$ and R$_m$ together form a C$_4$–C$_6$-alkylene bridge which may be interrupted by oxygen, NH or —N(C$_1$–C$_4$-alkyl)-;
R$_n$ represents C$_1$–C$_4$-alkyl, phenyl or halogen-, C$_1$–C$_4$-alkyl-, methoxy-, nitro- or trifluoromethyl-substituted phenyl;
R$_{38}$ represents hydrogen, C$_1$–C$_{10}$-alkyl, C$_1$–C$_4$-alkoxy-C$_1$–C$_4$-alkyl, C$_1$–C$_4$-alkylthio-C$_1$–C$_4$-alkyl, di-C$_1$–C$_4$-alkylamino-C$_1$–C$_4$-alkyl, halogeno-C$_1$–C$_8$-alkyl, C$_2$–C$_8$-alkenyl, halogeno-C$_2$–C$_8$-alkenyl, C$_3$–C$_8$-alkinyl, C$_3$–C$_7$-cycloalkyl, halogeno-C$_3$–C$_7$-cycloalkyl, C$_1$–C$_8$-alkylcarbonyl, allylcarbonyl, C$_3$–C$_7$-cycloalkylcarbonyl, benzoyl, which is unsubstituted or substituted up to three times on the phenyl ring by identical or different substituents from the group consisting of halogen, C$_1$–C$_4$-alkyl, halogeno-C$_1$–C$_4$-alkyl, halogeno-C$_1$–C$_4$-alkoxy and C$_1$–C$_4$-alkoxy; or represents furoyl, thienyl; or represents C$_1$–C$_4$-alkyl substituted by phenyl, halogenophenyl, C$_1$–C$_4$-alkylphenyl, C$_1$–C$_4$-alkoxyphenyl, halogeno-C$_1$–C$_4$-alkylphenyl, halogeno-C$_1$–C$_4$-alkoxyphenyl, C$_1$–C$_6$-alkoxycarbonyl, C$_1$–C$_4$-alkoxy-C$_1$–C$_8$-alkoxycarbonyl, C$_3$–C$_8$-alkenyloxycarbonyl, C$_3$–C$_8$-alkinyloxycarbonyl, C$_1$–C$_8$-alkylthiocarbonyl, C$_3$–C$_8$-alkenylthiocarbonyl, C$_3$–C$_8$-alkinylthiocarbonyl, carbamoyl, mono-C$_1$–C$_4$-alkylaminocarbonyl, di-C$_1$–C$_4$-alkylaminocarbonyl; or represents phenylaminocarbonyl which is unsubstituted or substituted up to three times on the phenyl by identical or different substituents from the group consisting of halogen, C$_1$–C$_4$-alkyl, halogeno-C$_1$–C$_4$-alkyl, halogeno-C$_1$–C$_4$-alkoxy and C$_1$–C$_4$-alkoxy or monosubstituted on the phenyl by cyano or nitro or represents dioxolan-2-yl which is unsubstituted or substituted by one or two C$_1$–C$_4$-alkyl radicals, or represents dioxan-2-yl which is unsubstituted or substituted by one or two $C_1$–$C_4$-alkyl radicals, or represents $C_1$–$C_4$-alkyl which is substituted by cyano, nitro, carboxyl or $C_1$–$C_8$-alkylthio-$C_1$–$C_8$-alkoxycarbonyl;

or a compound of the formula (IIf)

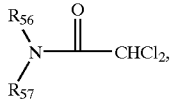

(IIf)

in which $R_{56}$ and $R_{57}$ independently of one another each represent $C_1$–$C_6$-alkyl or $C_2$–$C_6$-alkenyl; or $R_{56}$ and $R_{57}$ together represent

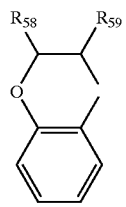

$R_{58}$ and $R_{59}$ independently of one another each represent hydrogen or $C_1$–$C_6$-alkyl; or $R_{56}$ and $R_{57}$ together represent

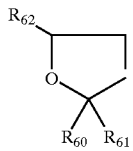

$R_{60}$ and $R_{61}$ independently of one another each represent $C_1$–$C_4$-alkyl, or $R_{60}$ and $R_{61}$ together represent —$CH_2)_5$—; $R_{62}$ represents hydrogen, $C_1$–$C_4$-alkyl or

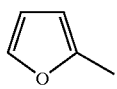

or $R_{56}$ and $R_{57}$ together represent

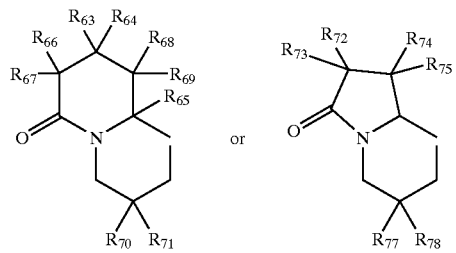

$R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$, and $R_{78}$ independently of one another each represent hydrogen or $C_1$–$C_4$-alkyl;

or a compound of the formula (IIg)

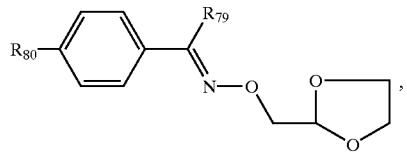

(IIg)

in which $R_{79}$ represents hydrogen or chlorine and $R_{80}$ represents cyano or trifluoromethyl, or a compound of the formula (IIh)

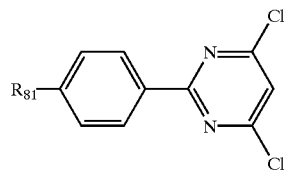

(IIh)

in which $R_{81}$ represents hydrogen or methyl, or of the formula (IIj)

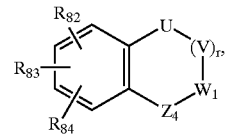

(IIj)

in which $R_{82}$ represents hydrogen, $C_1$–$C_4$-alkyl, $C_1$–$C_4$-alkyl substituted by $C_1$–$C_4$-alkyl-$X_2$— or $C_1$–$C_4$-halogenoalkyl-$X_2$—, represents $C_1$–$C_4$-halogenoalkyl, nitro, cyano, —$COOR_{85}$, —$NR_{86}R_{87}$, —$SO_2NR_{88}R_{89}$ or —$CONR_{90}R_{91}$;

$R_{83}$ represents hydrogen, halogen, $C_1$–$C_4$-alkyl, trifluoromethyl, $C_1$–$C_4$-alkoxy or $C_1$–$C_4$-halogenoalkoxy;

$R_{84}$ represents hydrogen, halogen or $C_1$–$C_4$-alkyl;

U, V, $W_1$ and $Z_4$ independently of one another each represent oxygen, sulphur, $C(R_{92})R_{93}$, carbonyl, $NR_{94}$, a group

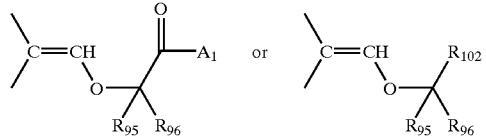

in which $R_{102}$ represents $C_2$–$C_4$-alkenyl or $C_2$–$C_4$-alkinyl;

with the proviso that a) at least one of the ring members U, V, $W_1$ or $Z_4$ is carbonyl and a ring member adjacent to this or these ring members represents the group

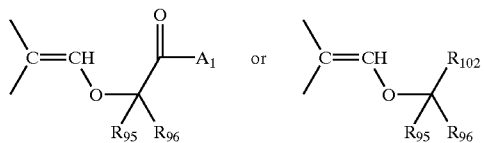

where this group occurs only once; and b) two adjacent ring members U and V, V and $W_1$ and $W_1$ and Z may not simultaneously represent oxygen;

$R_{95}$ and $R_{96}$ independently of one another each represent hydrogen or $C_1$–$C_8$-alkyl; or $R_{95}$ and $R_{96}$ together form a $C_2$–$C_6$-alkylene group;

$A_1$ is $R_{99}$-$Y_1$— or —$NR_{97}R_{98}$;

$X_2$ is oxygen or —$S(O)_s$;

$Y_1$ is oxygen or sulphur;

$R_{99}$ is hydrogen, $C_1$–$C_8$-alkyl, $C_1$–$C_8$-halogenoalkyl, $C_1$–$C_4$-alkoxy-$C_1$–$C_8$-alkyl, $C_3$–$C_6$-alkenyloxy-$C_1$–$C_8$-alkyl or phenyl-$C_1$–$C_8$-alkyl, where the phenyl ring may be substituted by halogen, $C_1$–$C_4$-alkyl, trifluoromethyl, methoxy or methyl-$S(O)_s$—, represents $C_3$–$C_6$-alkenyl, $C_3$–$C_6$-halogenoalkenyl, phenyl-$C_3$–$C_6$-alkenyl, $C_3$–$C_6$-alkinyl, phenyl-$C_3$–$C_6$-alkinyl, oxetanyl, furyl or tetrahydrofIryl;

$R_{85}$ represents hydrogen or $C_1$–$C_4$-alkyl;

$R_{86}$ represents hydrogen, $C_1$–$C_4$-alkyl or $C_1$–$C_4$-alkylcarbonyl;

$R_{87}$ represents hydrogen or $C_1$–$C_4$-alkyl; or $R_{86}$ and $R_{87}$ together form a $C_4$— or $C_5$-alkylene group;

$R_{88}$, $R_{89}$, $R_{90}$ and $R_{91}$ independently of one another each represent hydrogen or $C_1$–$C_4$-alkyl; or $R_{88}$ together with $R_{89}$ or $R_{90}$ together with $R_{91}$ independently of one another represent $C_4$— or $C_5$-alkylene, where one carbon atom may be replaced by oxygen or sulphur or one or two carbon atoms may be replaced by —$NR_{100}$—;

$R_{92}$, $R_{100}$ and $R_{93}$ independently of one another each represent hydrogen or $C_1$–$C_8$-alkyl; or $R_{92}$ and $R_{93}$ together represent $C_2$–$C_6$-alkylene;

$R_{94}$ represents hydrogen or $C_1$–$C_8$-alkyl;

$R_{97}$ represents hydrogen; $C_1$–$C_8$-alkyl, phenyl, phenyl-$C_1$–$C_8$-alkyl, where the phenyl rings may be substituted by fluorine, chlorine, bromine, nitro, cyano, —$OCH_3$, $C_1$–$C_4$-alkyl or $CH_3SO_2$—, represents $C_1$–$C_4$-alkoxy-$C_1$–$C_8$-alkyl, $C_3$–$C_6$-alkenyl or $C_3$–$C_6$-alkinyl;

$R_{98}$ represents hydrogen, $C_1$–$C_8$-alkyl, $C_3$–$C_6$-alkenyl or $C_3$–$C_6$-alkinyl, or $R_{97}$ and $R_{98}$ together represent $C_4$— or $C_5$-alkylene, where one carbon atom may be replaced by oxygen or sulphur, or one or two carbon atoms may be replaced by —$NR_{101}$—; $R_{101}$ represents hydrogen or $C_1$–$C_4$-alkyl;

r represents 0 or 1; and s represents 0, 1 or 2, or a compound of the formula (IIk)

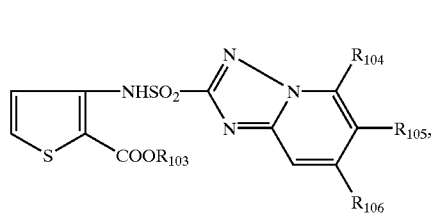

in which $R_{103}$ represents hydrogen, $C_1$–$C_6$-alkyl, $C_3$–$C_6$-cycloalkyl, $C_3$–$C_6$-alkenyl or $C_3$–$C_6$-alkinyl; and $R_{104}$, $R_{105}$ and $R_{106}$ independently of one another each represent hydrogen, $C_1$–$C_6$-alkyl, $C_3$–$C_6$-cycloalkyl or $C_1$–$C_6$-alkoxy, with the proviso that one of the substituents $R_{104}$, $R_{105}$ and $R_{106}$ is different from hydrogen, where generally from 0.001 to 1000 parts by weight of one of the abovementioned compounds of group (b) are present per part by weight of an active compound 2-(2-methoxycarbonyl-phenylsulphonylaminocarbonyl)-4-methyl-5-propoxy-2,4-dihydro-3H-1,2,4-triazol-3-one of the formula (I) or its salts.

Among the compounds of group (b) defined by the general formulae, preference is given to those which are listed in the tables below:

TABLE 1

Compounds of the formula (IIa)

(IIa)

| Comp. No. | $X_1$ | $R_{32}$ |
|---|---|---|
| 1.01 | Cl | —CH(CH$_3$)—C$_5$H$_{11}$-n |
| 1.02 | Cl | —CH(CH$_3$)—CH$_2$OCH$_2$CH=CH$_2$ |
| 1.03 | Cl | H |
| 1.04 | Cl | C$_4$H$_9$-n |

TABLE 2

Compounds of the formula (IIb)

(IIb)

| Comp. No. | $R_{38}$ | $R_{39}$ | $R_{40}$ | $R_{41}$ | E |
|---|---|---|---|---|---|
| 2.01 | CH$_3$ | phenyl | 2-Cl | H | CH |
| 2.02 | CH$_3$ | phenyl | 2-Cl | 4-Cl | CH |

TABLE 2-continued

Compounds of the formula (IIb)

(IIb)

| Comp. No. | $R_{38}$ | $R_{39}$ | $R_{40}$ | $R_{41}$ | E |
|---|---|---|---|---|---|
| 2.03 | $CH_3$ | phenyl | 2-F | H | CH |
| 2.04 | $CH_3$ | 2-chlorophenyl | 2-F | H | CH |
| 2.05 | $C_2H_5$ | $CCl_3$ | 2-Cl | 4-Cl | N |
| 2.06 | $CH_3$ | phenyl | 2-Cl | 4-$CF_3$ | N |
| 2.07 | $CH_3$ | phenyl | 2-Cl | 4-$CF_3$ | N |
| 2.08 | $CH_3$ | 2-fluorophenyl | 2-Cl | H | CH |

TABLE 3

Compounds of the formula (IIc)

(IIc)

| Comp. No. | $R_{29}$ | $R_{30}$ | $R_{31}$ | $R_{27}$ | $R_{28}$ |
|---|---|---|---|---|---|
| 3.01 | $CH_3$ | $CH_3$ | $CH_3$ | 2-Cl | 4-Cl |
| 3.02 | $CH_3$ | $C_2H_5$ | $CH_3$ | 2-Cl | 4-Cl |
| 3.03 | $CH_3$ | $C_2H_5$ | $C_2H_5$ | 2-Cl | 4-Cl |

TABLE 4

Compounds of the formula (IIe)

(IIe)

| Comp. No. | $A_2$ | $R_{14}$ |
|---|---|---|
| 4.001 | 2-methoxyphenyl | H |
| 4.002 | 2,4-dimethylphenyl | H |
| 4.003 | 1-methylnaphthyl | $CH_3$ |
| 4.004 | 2-methoxyphenyl | $CH_3$ |

TABLE 5

Compounds of the formula (IIf)

(IIf)

| Comp. No. | $R_{56}$ | $R_{57}$ | $R_{56} + R_{57}$ |
|---|---|---|---|
| 5.001 | $CH_2=CHCH_2$ | $CH_2=CHCH_2$ | — |
| 5.002 | — | — | 2,2-dimethyl-1,3-dioxolane ring |
| 5.003 | — | — | 2,2,4-trimethyl-1,3-dioxolane ring |
| 5.004 | — | — | cyclohexyl-substituted oxolane ring |

TABLE 5-continued

Compounds of the formula (IIf)

(IIf)

$R_{56}\text{-N(R}_{57}\text{)-C(O)-CHCl}_2$

| Comp. No. | $R_{56}$ | $R_{57}$ | $R_{56} + R_{57}$ |
|---|---|---|---|
| 5.005 | — | — | (cyclopentadienyl-CH(CH2CH3)-O-C(CH3)2-CH3) |
| 5.006 | — | — | (chroman-CH2-CH(CH3)-) |
| 5.007 | — | — | (pyrrolidinone-dimethyl-CH2-C(CH3)2-CH2CH3) |

TABLE 6

Compounds of the formula (IIg)

(IIg)

$R_{80}\text{-C}_6H_4\text{-C(R}_{79}\text{)=N-O-CH}_2\text{-CH(1,3-dioxolane)}$

| Comp. No. | $R_{80}$ | $R_{79}$ |
|---|---|---|
| 6.01 | H | CN |
| 6.02 | Cl | $CF_3$ |

TABLE 7

Compounds of the formula (IIh)

(IIh)

$R_{81}\text{-C}_6H_4\text{-(4,6-dichloropyrimidin-2-yl)}$

| Comp. No. | $R_{81}$ |
|---|---|
| 7.01 | H |
| 7.02 | $CH_3$ |

TABLE 8

Compounds of the formula (IIm)

(IIm)

| Comp. No. | $R_{82}$ | $Z_4$ | V | r |
|---|---|---|---|---|
| 8.001 | H | $\text{(CH}_3\text{)}_2\text{C=CH-C(H)(O-CH}_2\text{-)CH=CH}_2$ | O | 1 |
| 8.002 | H | $\text{(CH}_3\text{)}_2\text{C=CH-C(H)(O-CH}_2\text{-)COOCH}_3$ | O | 1 |
| 8.003 | H | $\text{(CH}_3\text{)}_2\text{C=CH-C(H)(O-CH}_2\text{-)C}\equiv\text{CH}$ | O | 1 |
| 8.004 | H | $\text{(CH}_3\text{)}_2\text{C=CH-C(H)(O-CH}_2\text{-)COOCH(CH}_3\text{)(CH}_2\text{)}_4\text{CH}_3$ | O | 1 |
| 8.005 | H | $\text{(CH}_3\text{)}_2\text{C=CH-C(H)(O-CH}_2\text{-)COOCH}_3$ | $CH_2$ | 1 |
| 8.006 | H | $\text{(CH}_3\text{)}_2\text{C=CH-C(H)(O-CH(CH}_3\text{)-)COOCH}_3$ | $CH_2$ | 1 |
| 8.007 | H | $\text{(CH}_3\text{)}_2\text{C=CH-C(H)(O-CH}_2\text{-)COOCH}_3$ | S | 1 |
| 8.008 | H | $\text{(CH}_3\text{)}_2\text{C=CH-C(H)(O-CH}_2\text{-)C}\equiv\text{CH}$ | S | 1 |
| 8.009 | H | $\text{(CH}_3\text{)}_2\text{C=CH-C(H)(O-CH}_2\text{-)C}\equiv\text{CH}$ | $NCH_3$ | 1 |
| 8.010 | H | $\text{(CH}_3\text{)}_2\text{C=CH-C(H)(O-CH}_2\text{-)COOCH}_3$ | $NCH_3$ | 1 |
| 8.011 | H | $\text{(CH}_3\text{)}_2\text{C=CH-C(H)(O-CH(CH}_3\text{)-)COOCH}_3$ | $NCH_3$ | 1 |
| 8.012 | H | $\text{(CH}_3\text{)}_2\text{C=CH-C(H)(O-CH(CH}_3\text{)-)COOCH}_3$ | O | 1 |

TABLE 8-continued

Compounds of the formula (IIm)

(IIm): R82—[benzene ring]—CH2—(V)r—Z4—C(=O) (fused)

| Comp. No. | R82 | Z4 | | V | r |
|---|---|---|---|---|---|
| 8.013 | H | | \C=CH—O—CH(CH3)—COOCH3 | S | 1 |

TABLE 9

Compounds of the formula (IIn)

(IIn): R82—[benzene ring]—U—C(=O)—Z4 (fused)

| Comp. No. | U | R82 | Z4 |
|---|---|---|---|
| 9.001 | O | H | \C=CH—O—CH2—C(H2)—COOCH3 |
| 9.002 | O | H | \C=CH—O—CH2—C≡CH |
| 9.003 | O | 5-Cl | \C=CH—O—CH2—COOCH3 |
| 9.004 | CH2 | H | \C=CH—O—CH2—COOCH3 |
| 9.005 | CH2 | H | \C=CH—O—CH2—COO—CH2—C6H5 |
| 9.006 | CH2 | H | \C=CH—O—CH2—COOC2H5 |
| 9.007 | NH | 5-Cl | \C=CH—O—CH(CH3)—COOCH3 |
| 9.008 | NH | 5-Cl | \C=CH—O—CH2—COOCH3 |
| 9.009 | NH | H | \C=CH—O—CH2—COOCH3 |
| 9.010 | NH | H | \C=CH—O—CH(CH3)—COOCH3 |
| 9.011 | NCH3 | H | \C=CH—O—CH(CH3)—COOCH3 |
| 9.012 | NCH3 | H | \C=CH—O—CH2—COOCH3 |

TABLE 10

Compounds of the formula (IIo)

(IIo): R82—[benzene ring]—U—(V)r—W1—Z4 (fused)

| Comp. No. | U | V | r | W1 | Z4 | R82 |
|---|---|---|---|---|---|---|
| 10.001 | O | C=O | 1 | \C=CH—O—CH2—C≡CH | CH2 | H |
| 10.002 | O | C=O | 1 | \C=CH—O—CH2—COOCH3 | CH2 | H |
| 10.003 | CH2 | C=O | 1 | \C=CH—O—CH(CH3)—COOCH3 | CH2 | H |
| 10.004 | CH2 | C=O | 1 | \C=CH—O—CH2—COOCH3 | CH2 | H |
| 10.005 | CH2 | CH2 | 1 | \C=CH—O—CH2—COOCH3 | C=O | H |
| 10.006 | CH2 | CH2 | 1 | \C=CH—O—CH(CH3)—COOCH3 | C=O | H |
| 10.007 | NCH3 | C=O | 1 | \C=CH—O—CH2—COOCH3 | CH2 | H |

TABLE 11

Compounds of the formula (IIp)

(IIp)

![structure]

| Comp. No. | R_{82} | W_1 |
|---|---|---|
| 11.001 | 6-Cl | \C=CH-O-CH_2-COOCH_3 |
| 11.002 | 6-Cl | \C=CH-O-CH(CH_3)-COOCH_3 |
| 11.003 | H | \C=CH-O-CH_2-C≡CH |
| 11.004 | H | \C=CH-O-CH(CH_3)-COOCH_3 |
| 11.005 | H | \C=CH-O-CH_2-COOCH_3 |

TABLE 12

Compounds of the formula (IIk)

(IIk)

![structure]

| Comp. No. | $R_{103}$ | $R_{104}$ | $R_{105}$ | $R_{106}$ |
|---|---|---|---|---|
| 12.01 | $CH_3$ | H | cyclopropyl | H |
| 12.02 | $CH_3$ | $C_2H_5$ | cyclopropyl | H |
| 12.03 | $CH_3$ | cyclopropyl | $C_2H_5$ | H |
| 12.04 | $CH_3$ | $CH_3$ | H | H |
| 12.05 | $CH_3$ | $CH_3$ | cyclopropyl | H |
| 12.06 | $CH_3$ | $OCH_3$ | $OCH_3$ | H |
| 12.07 | $CH_3$ | $CH_3$ | $OCH_3$ | H |
| 12.08 | $CH_3$ | $OCH_3$ | $CH_3$ | H |
| 12.09 | $CH_3$ | $CH_3$ | $CH_3$ | H |
| 12.10 | $C_2H_5$ | $CH_3$ | $CH_3$ | H |
| 12.11 | $C_2H_5$ | $OCH_3$ | $OCH_3$ | H |
| 12.12 | H | $OCH_3$ | $OCH_3$ | H |
| 12.13 | H | $CH_3$ | $CH_3$ | H |
| 12.14 | $C_2H_5$ | H | H | $CH_3$ |
| 12.15 | H | H | H | $CH_3$ |
| 12.16 | $CH_3$ | H | H | $CH_3$ |

Particular preference according to the invention is given to selective herbicidal compositions which are characterized in that they comprise an active compound combination comprising (a) 2-(2-methoxycarbonyl-phenylsulphonyl-aminocarbonyl)-4-methyl-5-propoxy-2,4-dihydro-3H-1,2,4-triazol-3-one of the formula (I)

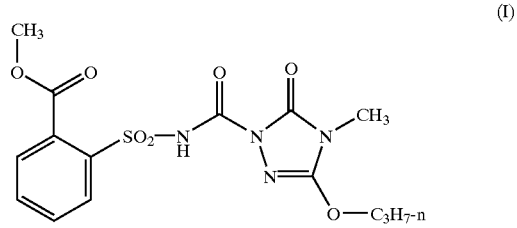

(I)

and/or one or more salts of the compound of the formula (I), in particular the sodium salt, and (b) diethyl 1-(2,4-dichlorophenyl)-4,5-dihydro-5-methyl-1H-pyrazole-3,5-dicarboxylate (mefenpyr-diethyl), 1-methylhexyl [(5-chloro-8-quinolinyl)oxy]acetate (cloquintocet-mexyl) and/or ethyl 1-(2,4-dichlorophenyl)-5-(trichloromethyl)-1H-1,2,4-triazole-3-carboxylate (fenchlorazole-ethyl), where in general from 0.001 to 1000 parts by weight of one of the abovementioned compounds of the group (b) are present per part by weight of an active compound 2-(2-methoxycarbonyl-phenylsulphonylaminocarbonyl)-4-methyl-5-propoxy-2,4-dihydro-3H-1,2,4-triazol-3-one of the formula (I).

Surprisingly, it has also been found that the herbicidally active substance 2,4-dichlorophenoxy-acetic acid (2,4-D) and its derivatives can also act as the abovementioned safener.

Another preferred embodiment is therefore a mixture comprising the compound of the formula (I) and/or its salts on the one hand and 2,4-D and/or its derivatives on the other hand. Typical derivatives of 2-4-D are, for example, its esters.

Among the compounds of the group (b), the compound diethyl 1-(2,4-dichlorophenyl)-4,5-dihydro-5-methyl-1H-pyrazole-3,5-dicarboxylate (mefenpyr-diethyl) is most preferred.

The compounds diethyl 1-(2,4-dichlorophenyl)-4,5-dihydro-5-methyl-1H-pyrazole-3,5-dicarboxylate (mefenpyr-diethyl), (1-methylhexyl) [(5-chloro-8-quinolinyl)oxy]acetate (cloquintocet-mexyl) and ethyl 1-(2,4-dichlorophenyl)-5-(trichloromethyl)-1H-1,2,4-triazole-3-carboxylate (fenchlorazole-ethyl) are described in the following patent applications: DE-A 39 395 03, EP-A 191 736 and DE-A 35 252 05, respectively. 2,4-D is a known herbicide.

Preferred salts of the compound of the formula (I) are the sodium, potassium, ammonium, methylammonium, ethylammonium, n- or i-propylammonium, n-, i-, s- or t-butylammonium, dimethylammonium, diethylammonium, di-n-propylammonium, di-i-propylammonium, di-n-butylammonium, di-i-butylammonium, di-s-butylammonium, trimethylammonium, triethylammonium, tripropylammonium, tributylammonium, trimethylsulphonium and triethylsulphonium salts.

Particularly preferred salts of compounds of the formulae (II) or (III) are the sodium, potassium, ammonium, methylammonium, ethylammonium, n- or i-propylammonium, dimethylammonium, diethylammonium, di-n-propylammonium, di-i- propylammonium and trimethylsulphonium salts, in particular the sodium salt.

Surprisingly, it has now been found that the above-defined active compound combinations of 2-(2-methoxycarbonyl-phenylsulphonylaminocarbonyl)-4-methyl-5-propoxy-2,4-dihydro-3H-1,2,4-triazol-3-one of the formula (I) or its salts and a safener/antidote from the group (b) listed above have, whilst being tolerated very well by crop plants, a particularly high herbicidal activity and can be used in various crops, in particular in cereals, especially wheat, but also in soya, potatoes, maize and rice.

Here, it has to be considered to be surprising that, from a large number of known safeners or antidotes which are capable of antagonizing the damaging effect of a herbicide on the crop plants, that are in particular the abovementioned compounds of group (b) which neutralize the damaging effect of 2-(2-methoxycarbonyl-phenylsulphonylaminocarbonyl)-4-methyl-5-propoxy-2,4-dihydro-3H-1,2,4-triazol-3-one and its salts, in particular its sodium salt, on the crop plants virtually completely without adversely affecting the herbicidal activity with respect to the weeds.

Emphasis is given here to the particularly advantageous effect of the particularly and most preferred combination partners from group (b), in particular in respect of sparing cereal plants, such as, for example, wheat, barley and rye, as crop plants. The active compound combinations according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalun, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compound combinations according to the invention is in no way restricted to these genera, but also extends in the same manner to other plants.

According to the invention, crop plants are all plants and plant varieties including transgenic plants and plant varieties.

The advantageous effect of the crop plant compatibility of the active compound combinations according to the invention is particularly highly pronounced at certain concentration ratios. However, the weight ratios of the active compounds in the active compound combinations can be varied within relatively wide ranges. In general, 0.001 to 1000 parts by weight, preferably 0.01 to 100 parts by weight, and particularly preferably 0.1 to 10 parts by weight of one of the compounds which improve crop plant compatibility mentioned under (b) above (antidotes/safeners) are present per part by weight of active compound of the formula (I) or its salts.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise from 0.1 to 95 per cent by weight of active compounds including the safeners, preferably between 0.5 and 90%.

The active compound combinations according to the invention are generally used in the form of finished formulations. However, the active compounds contained in the active compound combinations can also be mixed in individual formulations when used, i.e. in the form of tank mixes.

The novel active compound combinations, as such or in their formulations, can furthermore be used as a mixture with other known herbicides, finished formulations or tank mixes again being possible. A mixture with other known active compounds, such as fungicides, insecticides, acaricides, nematicides, bird repellents, growth factors, plant nutrients and agents which improve soil structure, is also possible. For certain intended uses, in particular in the post-emergence method, it may furthermore be advantageous to include, as further additives in the formulations, mineral or vegetable oils which are tolerated by plants (for example the commercial preparation "Oleo® DuPont 11E"), or ammonium salts such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. They are used in the customary manner, for example by pouring, spraying, atomizing, dusting or scattering.

The amounts of the active compound combinations according to the invention applied can be varied within a certain range; they depend, inter alia, on the weather and on soil factors. In general, the application rates are between 0.05 and 5 kg per ha, preferably between 0.05 and 2 kg per ha, particularly preferably between 0.1 and 1.0 kg per ha.

The active compound combinations according to the invention can be applied before and after emergence of the plants, that is to say by the pre-emergence and post-emergence method.

USE EXAMPLES

The active compounds in question were used in the form of customary formulations. The sodium salt of the compound of the formula (I) was applied as 70 WG or 70 WP, mefenpyr-diethyl was applied as 100 EC and fenchlorazole-ethyl and cloquintocetmexyl were applied as a laboratory formulation of the active compound produced by ourselves. The active compounds and, if appropriate, the safeners were used to prepare an aqueous spray liquor comprising 0.1% of the additive Renex-36.

Example A

Post-emergence Test

The active compound preparation is used to spray test plants which were grown in 10×10 cm pots (growth medium: soil or vermiculte), such that the particular amounts of active compound desired are applied per unit area. The concentration of the spray liquor is chosen such that the particular amounts of active compound desired are applied in 500 of water/ha.

After approximately 18 days the degree of damage to the crop plants was rated in % damage in comparison with the development of the untreated control.

The figures denote:

0%=no damage (like untreated control)

100%=total destruction/damage

Active compounds, application rates, test plants and results are shown in the tables below, the terms used in the tables having the following meaning:

wheat=wheat of the cultivar Orestis barley=barley of the cultivar Coronar a.i.=active ingredient=active compound/safener Sodium salt of the compound (I)=

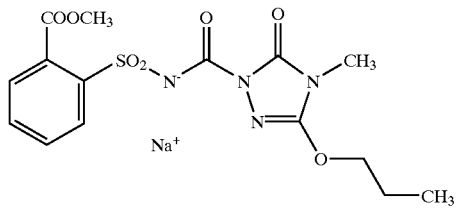

TABLE A1 post emergence test/greenhouse

| Active compound(s) | Application rate (g of a.i./ha) | Damage wheat [in %] |
|---|---|---|
| Sodium salt of the compound of the formula (I) | 180 | 30 |
|  | 90 | 20 |
| Sodium salt of the compound of the formula (I) + fenchlorazole-ethyl | 180 + 500 | 10 |
|  | 90 + 500 | 10 |
|  | 180 + 45 | 10 |
|  | 90 + 45 | 10 |

TABLE A2 post emergence test/greenhouse

| Active compound(s) | Application rate (g of a.i./ha) | Damage wheat [in %] |
|---|---|---|
| Sodium salt of the compound of the formula (I) | 250 | 50 |
|  | 125 | 30 |
|  | 60 | 20 |
| Sodium salt of the compound of the formula (I) + mefenpyr-diethyl | 250 + 250 | 20 |
|  | 125 + 125 | 0 |
|  | 60 + 60 | 0 |

TABLE A3 post emergence test/greenhouse

| Active compound(s) | Application rate (g of a.i./ha) | Damage wheat [in %] |
|---|---|---|
| Sodium salt of the compound of the formula (I) | 125 | 50 |
|  | 60 | 10 |
|  | 30 | 5 |
| Sodium salt of the compound of the formula (I) + mefenpyr-diethyl | 125 + 125 | 10 |
|  | 60 + 60 | 5 |
|  | 30 + 30 | 0 |

TABLE A4 post emergence test/greenhouse

| Active compound(s) | Application rate (g of a.i./ha) | Damage wheat [in %] |
|---|---|---|
| Sodium salt of the compound of the formula (I) | 125 | 40 |
|  | 60 | 30 |
| Sodium salt of the compound of the formula (I) + mefenpyr-diethyl | 125 + 250 | 10 |
|  | 60 + 250 | 0 |

TABLE A5 post emergence test/greenhouse

| Active compound(s) | Application rate (g of a.i./ha) | Damage barley [in %] |
|---|---|---|
| Sodium salt of the compound of the formula (I) | 60 | 70 |
| | 30 | 70 |
| | 15 | 50 |
| Sodium salt of the compound of the formula (I) + mefenpyr-diethyl | 60 + 60 | 60 |
| | 30 + 30 | 50 |
| | 15 + 15 | 30 |

TABLE A6 post emergence test/greenhouse

| Active compound(s) | Application rate (g of a.i./ha) | Damage barley [in %] |
|---|---|---|
| Sodium salt of the compound of the formula (I) | 60 | 60 |
| | 30 | 60 |
| | 15 | 50 |
| | 8 | 50 |
| Sodium salt of the compound of the formula (I) + mefenpyr-diethyl | 60 + 200 | 50 |
| | 30 + 200 | 30 |
| | 15 + 200 | 30 |
| | 8 + 200 | 5 |
| | 60 + 50 | 60 |
| | 30 + 50 | 40 |
| | 15 + 50 | 30 |
| | 8 + 50 | 10 |

TABLE A7 post emergence test/greenhouse

| Active compound(s) | Application rate (g of a.i./ha) | Damage wheat [in %] |
|---|---|---|
| Sodium salt of the compound of the formula (I) | 250 | 50 |
| | 125 | 30 |
| | 60 | 20 |
| Sodium salt of the compound of the formula (I) + chloquintocet-mexyl | 250 + 250 | 20 |
| | 125 + 125 | 10 |
| | 60 + 60 | 0 |

TABLE A8 post emergence test/greenhouse

| Active compound(s) | Application rate (g of a.i./ha) | Damage wheat [in %] |
|---|---|---|
| Sodium salt of the compound of the formula (I) | 125 | 50 |
| | 60 | 10 |
| | 30 | 5 |
| Sodium salt of the compound of the formula (I) + chloquintocet-mexyl | 125 + 125 | 10 |
| | 60 + 60 | 5 |
| | 30 + 30 | 0 |

TABLE A9 post emergence test/greenhouse

| Active compound(s) | Application rate (g of a.i./ha) | Damage barley [in %] |
|---|---|---|
| Sodium salt of the compound of the formula (I) | 60 | 70 |
| | 30 | 70 |
| | 15 | 50 |

TABLE A9-continued post emergence test/greenhouse

| Active compound(s) | Application rate (g of a.i./ha) | Damage barley [in %] |
|---|---|---|
| Sodium salt of the compound of the formula (I) + chloquintocet-mexyl | 60 + 60 | 60 |
| | 30 + 30 | 50 |
| | 15 + 15 | 30 |

What is claimed is:
1. A composition, comprising an effective amount of an active compound combination comprising
(a) 2-(2-methoxycarbonyl-phenylsulphonylaminocarbonyl)-4-methyl-5-propoxy-2,4-dihydro-3H-1,2,4-triazol-3-one of the formula (I)

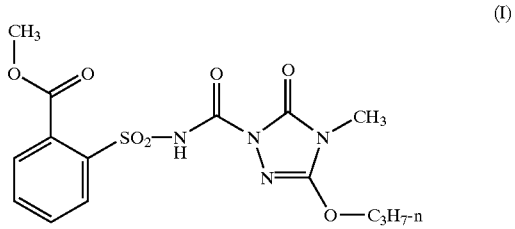

(I)

and/or one or more salts of the compound of the formula (I) and
(b) at least one crop plant compatibility-improving compound selected from the group consisting of
a compound of the formula (IIa),

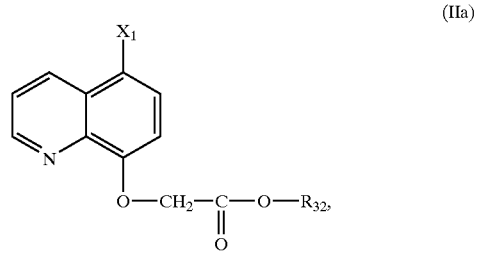

(IIa)

wherein
$R_{32}$ represents hydrogen, $C_1$–$C_8$-alkyl or $C_1$–$C_6$-alkoxy- or $C_3$–$C_6$-alkenyloxy-substituted $C_1$–$C_8$-alkyl and
X1 represents hydrogen or chlorine;
a compound of the formula (IIb)

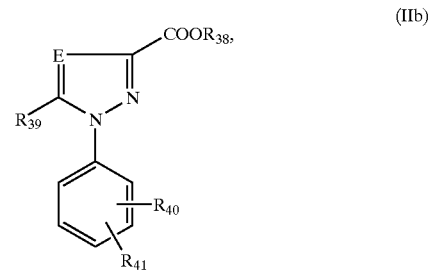

(IIb)

wherein
E represents nitrogen or methine;
$R_{38}$ represents $C_1$–$C_4$-alkyl;

$R_{39}$ represents —$CCl_3$, phenyl or halogen-substituted phenyl, and $R_{40}$ and $R_{41}$ independently represent hydrogen or halogen; or a compound of the formula (IIc)

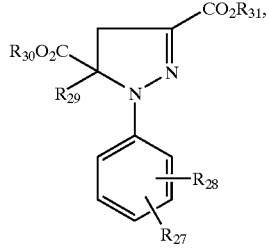

(IIc)

wherein $R_{27}$ and $R_{28}$ independently represent hydrogen or halogen and $R_{29}$, $R_{30}$ and $R_{31}$ independently represent $C_1$–$C_4$-alkyl.

2. The composition of claim 1, wherein from about 0.001 to about 1000 parts by weight of one of the compound of group (b) is present per part by weight of an active compound 2-(2-methoxycarbonyl-phenylsulphonylaminocarbonyl)4-methyl-5-propoxy-2,4-dihydro-3H-1,2,4-triazol-3-one of the formula (I) or its salt.

3. A method for controlling the growth of at least one plant comprising applying at least one composition of claim 1 to said plant and/or its habitat.

4. A process for preparing a herbicidal composition, comprising mixing at least one composition of claim 1 with at least one of surfactants and extenders.

5. A composition comprising an effective amount of an active compound combination comprising (a) 2-(2-methoxycarbonyl-phenylsulphonylaminocarbonyl)-4-methyl-5-propoxy-2,4-dihydro-3H-1,2,4-triazol-3-one of the formula (I)

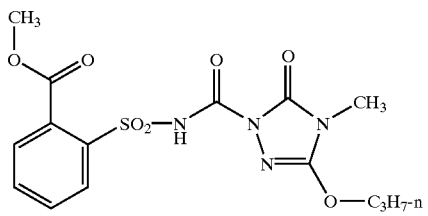

(I)

and/or one or more salts of the compound of the formula (I), and (b) least one crop plant compatibility-improving compound selected from the group consisting of diethyl 1-(2,4-dichlorophenyl)-4,5-dihydro-5-methyl-1H-pyrazole-3,5-dicarboxylate(mefenpyr-diethyl), 1-methylhexyl [(5-chloro-8-quinolinyl)oxy]acetate (cloquintocet-mexyl) and/or ethyl 1-(2,4-dichlorophenyl)-5-(trichloromethyl)-1H-1,2,4-triazole-3-carboxylate (fenchlorazole-ethyl).

6. The composition of claim 5, wherein component (b) is diethyl 1-(2,4-dichlorophenyl)-4,5-dihydro-5-methyl-1H-pyrazole-3,5-dicarboxylate (mefenpyr-diethyl).

7. The composition of claim 5, wherein from about 0.001 to about 1000 parts by weight of one of the compound of group (b) is present per part by weight of an active compound 2-(2-methoxycarbonyl-phenylsulphonylaminocarbonyl)-4-methyl-5-propoxy-2,4-dihydro-3H-1,2,4-triazol-3-one of the formula (I) or its salt.

8. A method for controlling the growth of at least one plant comprising applying at least one composition of claim 5 to said plant and/or its habitat.

9. A process for preparing a herbicidal composition, comprising mixing at least one composition of claim 5 with at least one of surfactants and extenders.

* * * * *